(12) United States Patent
Houde et al.

(10) Patent No.: US 8,123,423 B2
(45) Date of Patent: Feb. 28, 2012

(54) APPLICATOR WITH FLEXIBLE DISPENSING END

(75) Inventors: Ajay Houde, Duluth, GA (US); Susan Gayle Oslund, Roswell, GA (US); Tracy Joseph White, Loganville, GA (US); Wendy Anderson Cocke, Marietta, GA (US)

(73) Assignee: Kimberly-Clark Worlwide, Inc., Neenah, WI (US)

( * ) Notice: Subject to any disclaimer, the term of this patent is extended or adjusted under 35 U.S.C. 154(b) by 912 days.

(21) Appl. No.: 12/165,516

(22) Filed: Jun. 30, 2008

(65) Prior Publication Data

US 2009/0324319 A1    Dec. 31, 2009

(51) Int. Cl.
*B43K 5/00* (2006.01)

(52) U.S. Cl. ........ 401/205; 401/132; 401/138; 401/196; 401/198; 401/208; 401/218; 222/547; 222/566; 606/213; 606/214

(58) Field of Classification Search .................. 401/132, 401/133, 196, 198, 205, 206, 208, 209, 218, 401/137, 138; 222/546, 547, 566; 606/213, 606/214; 239/587.1, 588
See application file for complete search history.

(56) References Cited

U.S. PATENT DOCUMENTS

| | | | |
|---|---|---|---|
| 2,029,056 A | 1/1936 | Carlson | |
| 2,510,993 A | 6/1950 | Meyer | |
| 3,328,259 A | 6/1967 | Anderson | |
| 3,419,006 A | 12/1968 | King | |
| 3,560,100 A | 2/1971 | Spatz | |
| 4,147,775 A | 4/1979 | Schwartz et al. | |
| 4,192,299 A | 3/1980 | Sabatano | |
| 4,593,071 A | 6/1986 | Keough | |
| 4,799,815 A | 1/1989 | Barabino et al. | |
| 4,854,760 A | 8/1989 | Pike et al. | |
| 4,925,327 A | 5/1990 | Wirt | |
| 5,112,919 A | 5/1992 | Furrer et al. | |
| 5,288,159 A | 2/1994 | Wirt | |
| 5,529,577 A * | 6/1996 | Hammerslag | 606/214 |
| 5,658,384 A | 8/1997 | Imlay | |
| 6,054,523 A | 4/2000 | Braun et al. | |
| 6,214,332 B1 | 4/2001 | Askill et al. | |
| 6,342,213 B1 | 1/2002 | Barley et al. | |
| 6,425,704 B2 | 7/2002 | Voiers et al. | |
| 6,428,233 B1 | 8/2002 | Clark et al. | |
| 6,547,467 B2 | 4/2003 | Quintero | |
| 6,613,183 B2 | 9/2003 | Dewitt | |
| 6,616,019 B2 | 9/2003 | D'Alessio et al. | |
| 6,802,822 B1 | 10/2004 | Dodge | |

(Continued)

FOREIGN PATENT DOCUMENTS

EP    0639510 A2    2/1995

(Continued)

*Primary Examiner* — Steven J Ganey
(74) *Attorney, Agent, or Firm* — James B. Robinson; Sue C. Watson

(57) ABSTRACT

An applicator with a flexible dispensing end is provided. The applicator includes a housing having an internal compartment configured to hold a container of skin sealant. The housing includes a dispensing end having at least one opening to permit the skin sealant to be dispensed. The housing includes an actuator configured to contact the container and release the skin sealant. The dispensing end has at least one movable member. The dispensing end is flexible and is configured to move on more than one axis, and up to three axes, sequentially or simultaneously, so that the skin sealant dispensed from the applicator may be uniformly applied to contours on a patient's skin.

25 Claims, 4 Drawing Sheets

U.S. PATENT DOCUMENTS

| | | |
|---|---|---|
| 6,967,261 B1 | 11/2005 | Soerens et al. |
| 7,094,250 B2 | 8/2006 | Stenton |
| 7,168,878 B2 | 1/2007 | Tani |
| 7,946,453 B2 * | 5/2011 | Voegele et al. ............... 606/213 |
| 2004/0068218 A1 | 4/2004 | Davis et al. |
| 2007/0147947 A1 | 6/2007 | Stenton et al. |
| 2008/0046004 A1 | 2/2008 | Stenton |

FOREIGN PATENT DOCUMENTS

| | | |
|---|---|---|
| EP | 0992252 A2 | 4/2000 |
| WO | WO 2003/097157 | 11/2003 |
| WO | WO 2004/110545 A1 | 12/2004 |
| WO | WO 2005/030111 | 4/2005 |
| WO | WO 2006/049283 | 5/2006 |

* cited by examiner

APPLICATOR WITH FLEXIBLE DISPENSING END

BACKGROUND

Surgical site infections (SSI) occur following about 2-3 percent of surgeries in the United States with an estimated 500,000 incidents of SSI occurring annually, which can lead to significant patient morbidity and mortality. In addition to the negative impact of such infections on patient health, these potentially avoidable infections contribute significantly to the financial burden experienced by the health care system. SSIs result when an incision becomes contaminated by bacteria, and for most surgeries the primary source of these infection-causing microorganisms is the skin (an exception being surgeries in which the gastrointestinal tract is penetrated).

Various compositions are used to prepare the skin prior to surgery. Skin preparations or "preps" are used to remove some level of microbial load on the skin prior to making an incision. Skin sealant materials are used to protect patients from bacterial infections associated with surgical site incisions and insertion of intravenous needles. Skin preps are applied to the skin and allowed to dry to maximize effectiveness for reducing microorganisms. After the skin prep has dried, the sealant may be applied directly to the skin in liquid form. The sealant forms a coherent film with strong adhesion to the skin through various techniques based on the chemistry of the sealant composition.

Skin preps currently are predominantly povidone-iodine or chlorhexidine gluconate based formulations and may contain alcohol for fast drying and more effective killing of organisms. Time constraints in the operating room and the lack of an indicator that the prep has dried often result in the skin remaining wet when draping and/or surgery begin, creating the possibility of infection.

Skin sealants now use a polymer composition that dries to form a film through evaporation of a solvent, for example. Other skin sealants contain monomeric units that polymerize in situ to from a polymeric film. Cyanoacrylate sealants containing 2-cyanoacrylate monomer are an example of the latter type wherein the monomer polymerizes in the presence of a polar species such as water or protein molecules to form an acrylic film. The resulting film formed serves to immobilize bacterial flora found on the skin and prevents their migration into an incision made during a surgical procedure or skin puncture associated with insertion of an intravenous needle.

In some cases, a skin sealant may also encompass substances designed to protect or treat the nails or mucosal surfaces of the body. Such substances include nail polish, eyedrops, nasal sprays, etc and serve to provide an additional barrier between the skin and the environment.

Skin sealants may contain additives such as plasticizing agents to improve film flexibility and conformance, viscosity modifiers to aid in application of the liquid composition, free radical and anionic scavengers to stabilize the product prior to use, biocidal agents to kill immobilized bacteria under the film, and the like.

Skin sealants are conventionally placed in dispensers or applicators until they are needed. One exemplary applicator has the liquid sealant held in at least one oblong glass ampoule within a rigid nylon housing. The housing has a body and a cap that are slidably connected and it is the cap which holds the ampoule(s). In use, the two parts are moved toward each other to dispense the liquid; the cap moving into the body. Moving the parts together results in breakage of the glass ampoule(s) and dispensing of the liquid. A detent-type locking mechanism holds the body and cap together once they are moved. The locking mechanism consists of slots formed in the cap into which fits a slight protuberance or knoll of plastic formed on the inside surface of the body. Once the ampoule is broken, the liquid travels through a small piece of foam which catches any glass shards that may have been formed by the breakage of the ampoule and thence on to the tip portion of the body. The tip has a number of small holes in it to allow the liquid to pass through. The body of the tip has a piece of foam or sponge on the outside, which is often held in place with a rigid plastic oval-shaped ring that snaps in place on the tip. The outer foam contacts the skin of the patient when the liquid is dispensed. Other types of applicators or dispensers may be found in U.S. Pat. Nos. 7,094,250, 4,854,760, 4,925,327 and 5,288,159, and U.S. Patent Application Publication Nos. US2007/0147947 and 2008/0046004, all of which are incorporated herein by reference for all purposes.

In using the applicator, a user positions the dispensing end, which has the foam or sponge saturated with skin sealant, against a selected area of a patient's prepped skin. Stroking the dispensing end against the patient's skin, a user disposes the skin sealant thereon. It is desirable to uniformly apply the liquid skin sealant to the skin so that a uniform layer is formed on the skin to protect an incision, and so forth, from the migration of bacterial flora from the skin to the incision. There are several problems, however, with existing dispensing ends which can negatively impact the skin sealant's ability to immobilize bacterial flora found on the skin and prevent their migration into an incision made during a surgical procedure, a skin puncture associated with insertion of an intravenous needle, or a wound.

The dispensing end of the applicator is generally relatively rigid. Such rigidity works reasonably well on a relatively flat surface, such as a patient's abdomen. Problems occur, however, when using the applicator to apply skin sealant to angles, convexities, concavities, and so forth, such as those which are present about a bended knee, bended elbow, fingers, and so forth. In this instance, because of the rigidity of the dispensing end of the applicator, a smooth, even and regular layer of skin sealant is very difficult or impossible to apply. This is due to the fact that the dispensing end of the applicator does not flex or bend sufficiently to permit the application of the skin sealant evenly and uniformly into concave areas, such as behind a bended knee, or convex areas, such as over and around a knee cap, and so forth. Therefore, coverage by the skin sealant is likely to be non-uniform, therefore reducing the ability of the skin sealant to trap and immobilize bacterial flora. Further, the rigid dispensing end of the applicator, when used aggressively by a user over a convex or concave area, may create small scrapes or abrasions, even though the dispensing end may be covered by a foam or sponge. Such abrasions permit bacterial flora trapped on the skin below the skin sealant to migrate into the body via such abrasions. Further, the dispensing end, due to the sponge or foam on the dispensing end, cannot be used over sutures or staples covering an incision. This is due to the foam or sponge catching upon and pulling the sutures or staples. When pulled, the suture line may open slightly, again permitting an introduction of bacterial flora into the wound.

Therefore, there is a need for a dispensing end of a skin sealant applicator which is sufficiently flexible, so that skin sealant may be easily applied to concave and/or convex areas on a patient's body. Further, there is a need for a dispensing end on a skin sealant applicator which prevents abrasion of a patient's skin by over-zealous application of the skin sealant therein, or by application of too much pressure against the skin combined with a sharpness of a tip on the dispensing end.

Further, such a liquid applicator would desirably provide a smooth and even distribution of the skin sealant over the chosen skin surface. Finally, there is a need for a dispensing end of a skin sealant applicator for skin sealant which permits the application of the skin sealant over an insertion site of a needle or an incision closed by sutures and/or staples, without catching or pulling the sutures or staples.

SUMMARY OF THE INVENTION

In response to the difficulties and problems discussed herein, an applicator for a skin sealant is provided. The applicator has an applicator housing formed to include an internal compartment configured to hold a container of skin sealant. The housing includes a dispensing end having at least one opening formed therethrough. The housing also includes an actuator configured to contact the container and release the skin sealant. The dispensing end has at least one movable member such that the dispensing end is flexible and is configured to move on more than one axis when the dispensing end is positioned against a patient's skin.

In another aspect of the invention, an applicator for a skin sealant is provided. The applicator includes an applicator housing formed to include an internal compartment configured to hold a container of skin sealant. The housing includes a dispensing end having at least one opening formed therethrough. The housing also includes an actuator configured to contact the container and release the skin sealant. The dispensing end has at least one movable member such that the dispensing end is flexible and is configured to move on more than one axis when the dispensing end is positioned against a patient's skin. The dispensing end further comprises a porous roller having a plurality of openings formed therethrough. The roller is rotatably held by the dispensing end of the housing. When the skin sealant is released from the container, it flows through the plurality of openings in the roller and the at least one opening surrounding the roller in the dispensing end. The roller is positioned so that when the roller on the dispensing end of the applicator is stroked against a patient's skin, the skin sealant flows around and through at least a portion of the roller such that the skin sealant is uniformly dispensed on a patient's skin via the roller. Pressure applied to the roller and the dispensing end by a user when applying the skin sealant on a patient's skin does not result in abrasions on the patient's skin.

In yet another aspect of the invention, an applicator for a skin sealant is provided. The applicator includes an applicator housing formed to include an internal compartment configured to hold a container of skin sealant. The housing includes a dispensing end having at least one opening formed therethrough. The housing also includes an actuator configured to contact the container and release the skin sealant. The dispensing end has at least one movable member such that the dispensing end is flexible and is configured to move on up to three axes sequentially or simultaneously.

DEFINITIONS

Figure 1:
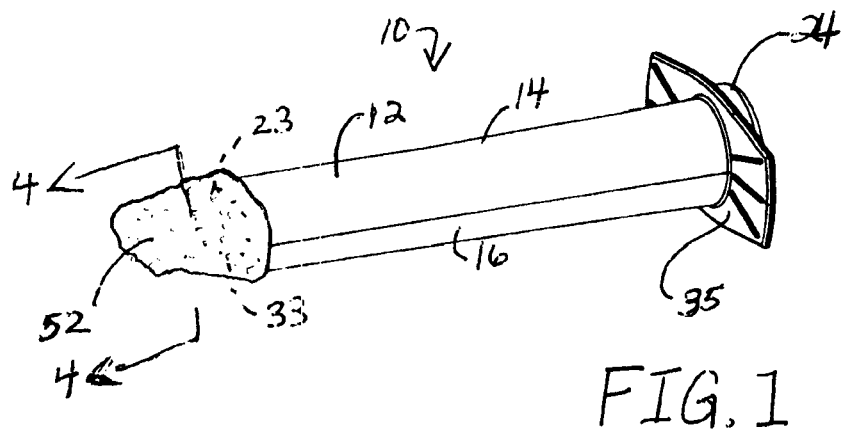
FIG. 1 is a perspective view of an applicator with a flexible dispensing end of the present invention.

As used herein the following terms have the specified meanings, unless the context demands a different meaning, or a different meaning is expressed; also, the singular generally includes the plural, and the plural generally includes the singular unless otherwise indicated.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the term "porous" refers to admitting the passage of gas or liquid through pores or openings through a component, such as the roller described herein. The roller is formed to include at least one opening, and desirably contains a plurality of openings.

As used herein, the term "unitary" refers to a unitary component, i.e., a whole, un-divided, un-separated component formed from one piece of material(s).

As used herein, the term "about" adjacent to a stated number refers to an amount that is plus or minus ten (10) percent of the stated number.

As used herein, the term "movable member" refers to one or more detents, one of more convexities, or both, which are provided on the dispensing end of the applicator, and which permit at least a portion of the dispensing end to lengthen or expand, to shorten or compress, to bend, flex and deflect such that the dispensing end, or at least a portion thereof, is movable in a vertical axis, a horizontal axis, and an oblique axis, sequentially or simultaneously.

These terms may be defined with additional language in the remaining portions of the specification.

DETAILED DESCRIPTION OF THE INVENTION

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 2:
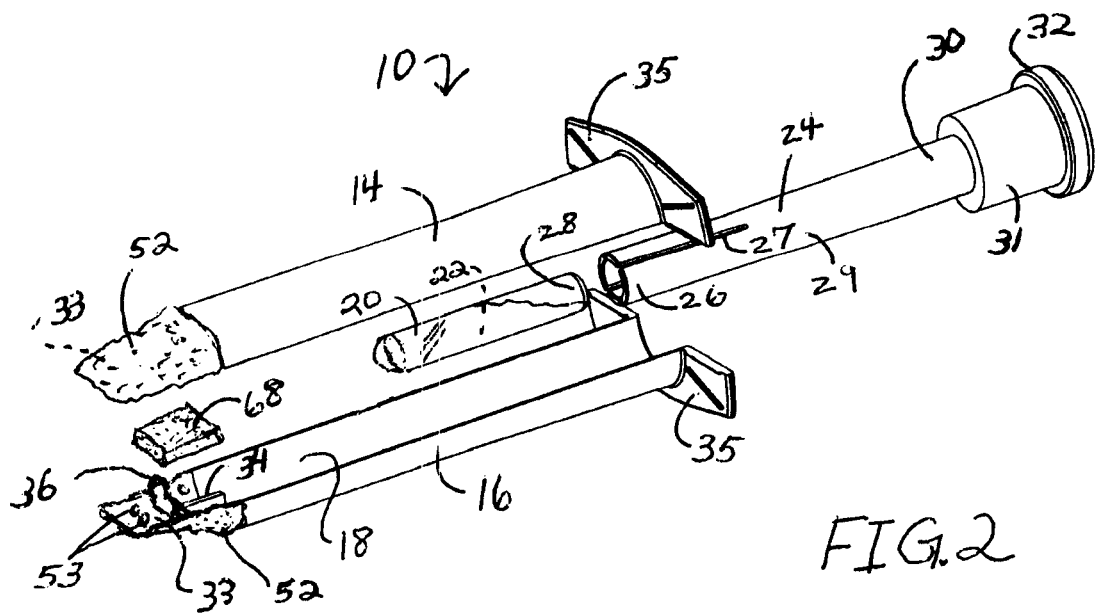
FIG. 2 is an exploded perspective view of the applicator of FIG. 1, showing the first and second side walls of the applicator which, when joined together, provide an applicator housing, as well as the plunger, and the container of skin sealant.
Figure 3:
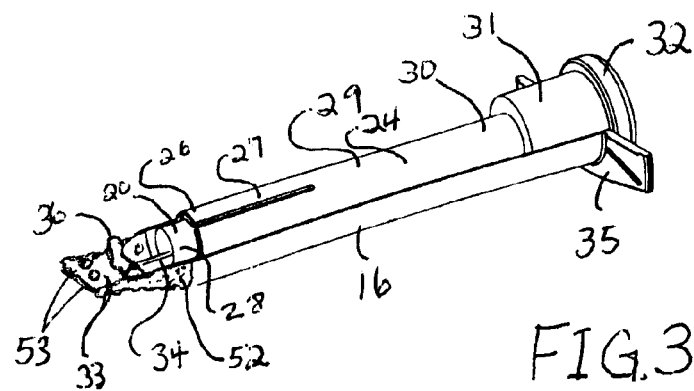
FIG. 3 is a perspective view of the porous applicator of FIG. 1, but showing the first side wall removed, and showing the position of the plunger and the container pushed against a rib adjacent a flexible dispensing end, an end of the container opened or ruptured to permit skin sealant to flow to the flexible dispensing end and the foam covering disposed thereon.

Turning now to the drawings as illustrated in FIGS. 1-10, and in particular, to FIGS. 1-5, an applicator for a skin sealant is provided. As shown in FIGS. 1-3. The applicator 10 includes a housing 12. The housing 12 has a first side wall 14 and a second side wall 16 which are configured to be coupled together to provide the housing 12. The housing 12 has a generally hollow internal compartment 18, which is configured to hold a container 20 having a skin sealant 22 therein. The housing also includes a dispensing end 23 from which the skin sealant 22 is dispensed.

Figure 5:
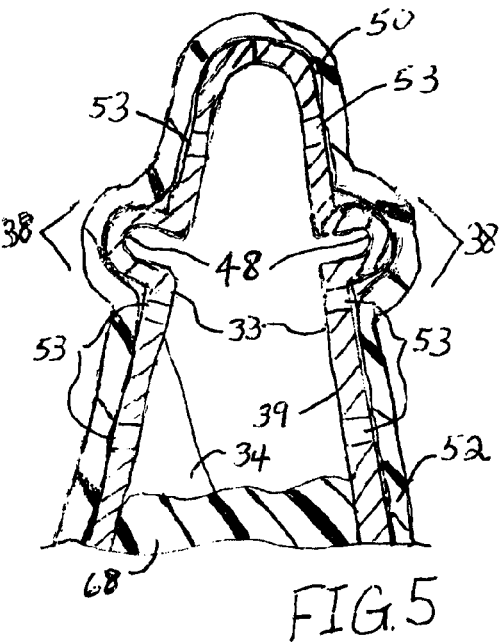
FIG. 5 is a cross-sectional view similar to FIG. 4, but showing an alternative flexible dispensing end.
Figure 6:
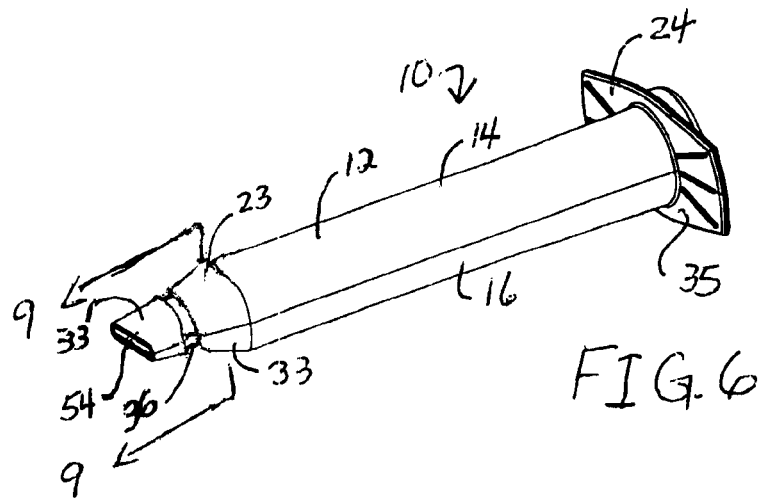
FIG. 6 is a perspective view of another embodiment of the applicator with a flexible dispensing tip.
Figure 7:
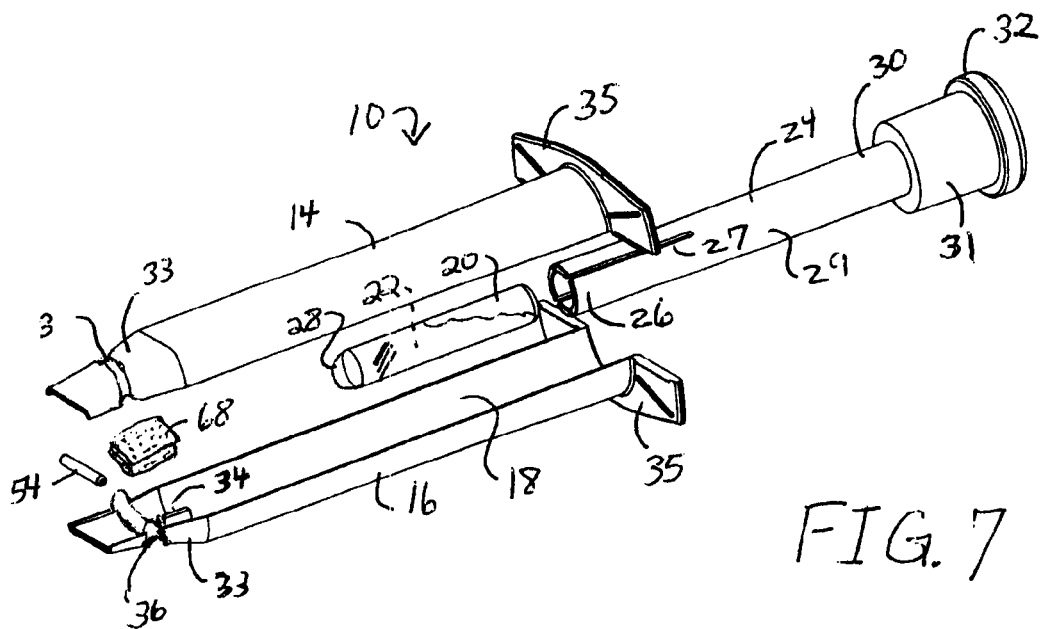
FIG. 7 is an exploded perspective view of the applicator of FIG. 6, but showing the flexible dispensing tip with a porous roller on the dispensing end thereof.

The housing 12 also desirably includes a means 24 for releasing the skin sealant from the container 20, as shown in FIGS. 2 and 5. Such means may include an actuator or a plunger 24 to permit such release. The actuator of plunger 24 has a first end 26 which may include a slit therein 27. The first end 26 is desirably configured to extend into the internal compartment 18 of the housing 12 and engage an end 28 of the container 20. A plunger body 29 extends from the first end 26 to an opposite second end 30 of the plunger 24. The second end 30 may include a boss 31 positioned thereon which may have a radially-extending outer ring 32. The housing 12 desirably may include an opening (not shown) for the plunger 24. The internal compartment 18, the container 20, and the plunger 24 may cooperate such that when the plunger 24 causes an opening or rupture of the container 20, the skin sealant 22 contained therein is flows out of the container 20 and toward a dispensing end of the housing 12 in order to be dispensed therefrom, as will be described in greater detail below. Due to the cooperation of these components, however, the skin sealant 22 is substantially prevented from flowing into other areas of the internal compartment 18, so that the skin sealant 22 is substantially and effectively dispensed from the dispensing end 23 of the housing 12.

The means 24 for releasing the skin sealant from the container 20, that is, an actuator, may also include additional or different components. For example, but not by way of limitation, a button (not shown) may be formed in any portion of the housing 12. The button may be configured to contact the container to cause a breach, breakage, or other opening in the container such that skin sealant is released therefrom. A latch or lever (not shown) may be provided, which, when moved or actuated, results in the release of the skin sealant from the container. The housing may include a hinge (not shown) or, alternatively, be formed to include a deformable section (not shown), so that when pushed or pressed, the skin sealant is released from the container. It will be understood that the container may be pushed, pulled, pressed, crushed, breached, broken, torn, impaled, cut, squeezed, opened, and so forth, to permit release of the skin sealant from the container.

The first and second side walls 14, 16 each have a tapered portion 33 at one end. At least one tapered portion 33 of at least one of the side walls 14, 16 may include at least one rib 34 positioned therein. Alternatively, the rib may be positioned on more than one side wall(s) (not shown). The first and second sidewalls 14, 16 may also include a flange portion 35 which extends outward, away from the side walls 14, 16, generally, but not by way of limitation, at an angle, such as, for example only, about a ninety (90) degree angle. When the side walls 14, 16 are coupled together to form the housing 12, the housing 12 has an opening which permits the actuator or plunger 24 to be positioned within the internal compartment 18. The flange portion 35 acts as a stop against the outer ring 32 of the boss 31, thereby preventing an over-extension of the actuator or plunger 24 into the housing 12.

The housing 12 may have various latches and detents (not shown) which permit the components of the housing 12 to be coupled and/or to form the housing 12. Further, the housing 12 may include one or more locking mechanisms (not shown) such that one or more components of the housing may be locked (releaseably or non-releaseably) into a position. In addition, the shape of the housing 12 is intended as non-limiting, and any housing shape may be utilized, so long as the housing operates as shown and/or described herein. Moreover, the housing may comprise a single unitary component formed from a single piece of material (not shown). Alternatively, the housing may be constructed from a number of components that are coupled together to form the housing. In particular, the tapered portions 33 which provide at least a portion of the dispensing end 23 may be formed totally, partially, or separately from the side walls 14, 16.

Figure 4:
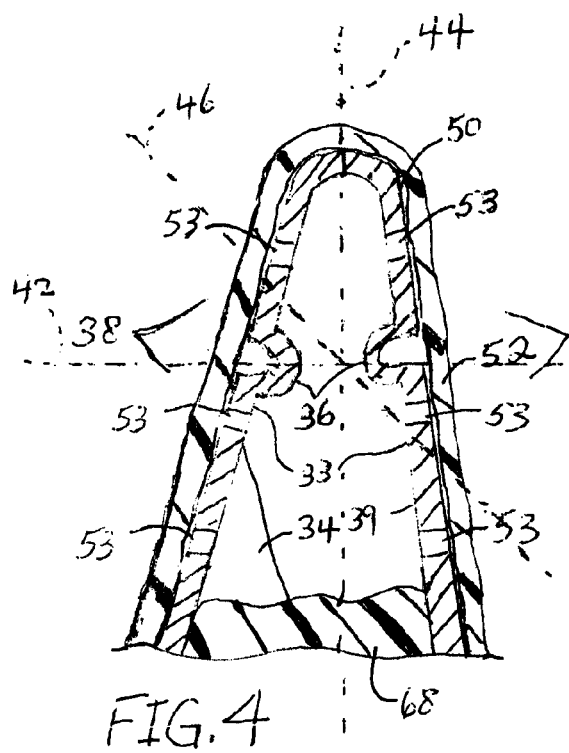
FIG. 4 is a cross-sectional view of FIG. 1, showing the flexible dispensing end.

Turning to the tapered portions 33, a movable member or detent 36 may be formed through a surface of at least a portion of the tapered portions 33, as illustrated in FIG. 4. Desirably, such a detent 36 will extend about the tapered portions 33, and may, by way of non-limiting example, form a ring about the tapered portions 33. The tapered portions 33, or at least a portion 38 thereof defined by one of more detents 36, are desirably formed on an inner surface 39 from a flexible and resilient material. Such a flexible material permits bending, flexing and deflection of the portion 38 along a horizontal axis 42, a vertical axis 44, and/or an oblique axis 46 (FIG. 4). Such a flexible and resilient material desirably has a memory, wherein once the tapered portions 33 have bent, flexed and/or deflected along one, two or three axis, the tapered portions 33 return to their previous shape and position. The flexible material is desirably formed from a material which does not unduly interfere with the skin sealant 22, and does not unduly affect the curing of the skin sealant 22. The dispensing end 23 may move in accordance with one axis, two axes, or all three axes, either sequentially or simultaneously.

It will e appreciated that a plurality of movable members or a plurality of detents may be utilized in the dispensing end 23 of the applicator. This plurality of detents 36 provide the tapered portions 33 of the dispensing end 23 of the applicator 10 with even more flexibility.

Alternatively, the tapered portions 33 may include one or more movable members or convexities 48 on an outer surface 50 thereof, such as, as illustrated in FIG. 5, a convexity 48 or a plurality of convexities (not shown) operate in a manner similar to that of the detents 36, and is formed from one or more flexible, resilient materials that bend, flex and deflect as described previously herein. In yet another alternative, the tapered portions 33 combine one or more detents as well as one or more convexities (not shown) from a flexible and resilient material, to provide even further adaptability to a surface, such as, for example only, a patient's bent knee area. Such detents 36 and/or convexities 48 permit at least the portion 38 of the dispensing end to flex, bend or move within one or more axes 42, 44 46 (FIG. 4). Such movable members, i.e., one or more detents and/or one or more convexities, permit at least a portion of the dispensing end 23 to move on one axis, two axes, or three axes, sequentially or simultaneously. The movable members or detents and convexities may comprise an accordion-shape (not shown).

A sponge or foam 52 may be used at the dispensing end 23, as illustrated in FIGS. 1-5. The dispensing end 23 desirably includes a plurality of apertures 53 formed therethrough. The plurality of apertures 53 permit the skin sealant 22 to flow out of the dispensing end 23 and onto the sponge 52. The flexibility of the material along with the dispensing end 23 along with the sponge 52 may assist in preventing a user from inadvertently causing abrasions on a patient's skin when applying the skin sealant. The use of a sponge of foam 52 on the dispensing end 23 continues to be a problem when the skin sealant is applied to a wound or incision closed by sutures or staples (not shown). In this instance, it would be desirable to use an alternative dispensing end 23 which utilizes one or more detents 36 and/or one or more convexities 48 along with a porous roller 54. Such an embodiment does not require the sponge 52 positioned on the outer surface 50 of the dispensing end 23. In this embodiment, the skin sealant is dispensed via the roller 54 positioned in an opening in the dispensing end 23 (FIGS. 6-10). The movable member or detent(s) 36 and/or convexity(ies) 48 permit the dispensing end 23 to expand, contract, bend, flex and/or deflect in up to three axes 42, 44, 46 (FIG. 4), while the porous roller 54 allows uniform and even distribution of the skin sealant 22 without catching or tearing sutures or staples.

Figure 8:
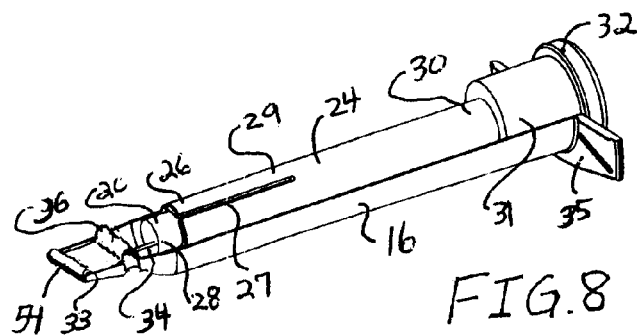
FIG. 8 is a perspective view of the applicator of FIG. 6, but showing the first side wall removed, and showing the position of the plunger and the container pushed against a rib adjacent the flexible dispensing end, an end of the container opened or ruptured to permit skin sealant to flow to the flexible dispensing end and the porous roller held therein.
Figure 9:
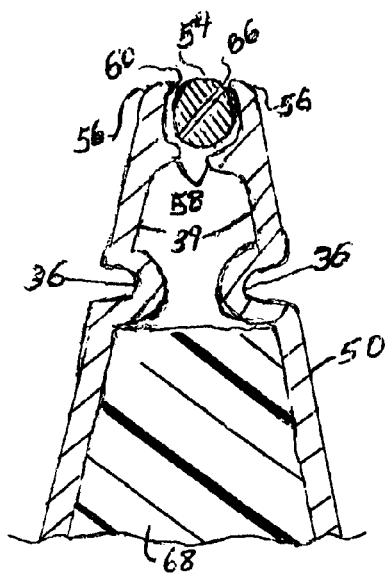
FIG. 9 is a cross-sectional view of FIG. 6 at lines 6-6, showing the porous roller positioned in an opening in the flexible dispensing end.

In the above-referenced alternate embodiment, desirably, but not by way of limitation, a cylindrical porous roller 54 is desirably positioned between smooth ends 56 of the tapered portions 33, as illustrated in FIGS. 8 and 9. A lip 58 formed on the inner surface 39 of each tapered portion 33 also holds the roller 54. When the first and second sidewalls 14,16 are positioned together to provide the housing 12, the tapered portions 33 cooperate to provide the tapered dispensing end 23 for the applicator 10. The roller 54 is held in a rolling dispensing position on the dispensing end 23 via cooperation between each smooth end 56 of each tapered portion 33 and each lip 58 on the inner surface 39 of each tapered portion 33. Each smooth end 56 of each tapered portion 33 is disposed a distance apart, but is positioned to prevent the roller 54 from moving away from the dispensing end 23. The cooperating smooth ends 56 provide a slot 60 between the tapered portions 33. This slot 60 is mostly filled with the roller 54 which extends a short distance outward and away from the tapered dispensing end 23, and the slot 60 forms at least a portion of an exit port through which the skin sealant 22 flows.

Figure 10:
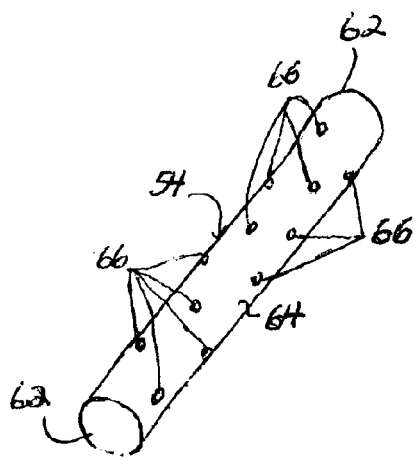
FIG. 10 is a perspective view of the roller of FIGS. 6-9, showing the plurality of openings therein.

The roller 54 includes a pair of spaced-apart ends 62. A cylindrical body 64 is positioned between the ends 62, and may includes at least one opening 66 formed transversly through the cylindrical body 64. Desirably, however, the cylindrical body 64 includes a plurality of openings 66 formed transversely therethrough, as illustrated in FIG. 10. The openings 66 are desirably sized so that the skin sealant flows therethough. The cylindrical body 64 may be substantially solid. Alternatively, the cylindrical body 64 may be hollow (not shown). In yet another alternative, the cylindrical body may be formed without one or a plurality of openings (not shown).

The shape of the roller 54 is intended as non-limiting. Therefore, by way of non-limiting example, a spherically-shaped roller (not shown), an elliptically-shaped roller (not shown), or any shape of roller which permits the applicator to function as shown and/or described herein may be utilized. In this circumstance, it will be understood that the applicator housing will be modified accordingly to accommodate the shape of the roller. Desirably, such rollers may be supplied with openings formed therethrough. Alternatively, such rollers may be supplied without openings.

A liquid permeable sponge or foam 68 is desirably positioned between the container 20 and the dispensing end 23, to prevent any portion of the container 20 from being dispensed through the dispensing end 23. Alternatively, another liquid permeable material (not shown) may be positioned between the container and the dispensing end, to prevent dispensing of any piece of the container. In yet another alternative, a liquid permeable material may be disposed about the container, to prevent pieces or particles of a broken container from being dispensed through the dispensing end. In yet another alternative, the components of the applicator and openings provided therein may be constructed to prevent particles or pieces of a broken container from being dispensed through the dispensing end. The container is desirably constructed from glass, plastic, or any material which does not react to the liquid skin sealant contained therein, so that the skin sealant is not permitted to prematurely cure or dry within the container. In addition, in yet another alternative, the housing may be formed to provide a part or all of the container (not shown).

As noted previously herein, prior to application of a skin sealant to a patient's skin, the skin over and in the area in which an incision will be made during a medical or surgical procedure is cleansed by the use of a skin preparation. Skin preparations or "preps" are used to remove some level of microbial load on the skin prior to making an incision. Skin preps are applied to the skin and allowed to dry to maximize effectiveness for reducing microorganisms. Skin preps currently are predominantly povidone-iodine or chlorhexidine gluconate based formulations and may contain alcohol for fast drying and more effective killing of organisms. Povidone iodine, available commercially as Betadine® is estimated to be used in 80 percent of surgeries as a skin preparation. Betadine® skin prep is an aqueous solution of 10 percent povidone iodine having 1 percent titratable iodine content. When Betadine® skin prep is applied to the skin, it imparts an orange-brown see-through color tint. It is necessary to permit the skin prep to completely dry, before the skin sealant is applied to the prepped skin.

In a method of use of the embodiment of an applicator with a flexible dispensing end 23 illustrated in FIGS. 1-5, the container 20 of skin sealant 22 is desirably positioned within the internal compartment 18 of the housing 12. The actuator or plunger 24 is positioned in the housing 12 and pushed inward into the internal compartment 18 such that the first end 26 of the actuator or plunger 24 ruptures the container 20 against the rib 34 or other apparatus. This action permits the skin sealant 22 to be released to the dispensing end 23. The actuator or plunger 24 is desirably moveable within the housing 12 until the ring 32 on the boss 31 of the plunger 24 rests against the flange portion 35, which acts as a stop to the actuator or plunger 24.

The skin sealant 22, when released from the container 20, flows via gravity through the sponge 68 (or other material) in the internal compartment 18 of the dispensing end 23 and through the plurality of apertures 53 formed therethrough. The skin sealant 22 therefore flows though the plurality of apertures 53 and onto the sponge 52 positioned over the dispensing end 23. The sponge 52 may be formed as a single component (FIG. 1). Alternatively, the sponge 52 may be formed from more than one piece (FIGS. 2-3). When a user presses the sponge 52 covering the dispensing end 23 against a prepped area of a patient's skin having contours (i.e., areas having one or move convexities and/or one or more concavities), the dispensing end 23 via the detent(s) 36 (FIG. 4), the convexity(ies) 48 (FIG. 5) or both (not shown) are evenly and uniformly covered by the skin sealant due to the movability, namely, the compression, extension, flexing, bending, and/or deflecting of the dispensing end 23 of the applicator 10 via the movable member(s) 36 and/or 48.

In another method of use of the embodiment of the present invention shown in FIGS. 6-10, the skin sealant 22, when released from the container 20, flows via gravity through the sponge 68 (or any material described herein for this purpose) to the dispensing end 23 and through the slot 60 therein and through the openings 66 in the roller 54. The sponge 68 desirably retain any broken portions of the container 20. Further, the roller 54 and the narrow slot 60 positioned about the roller 54, as well as the small openings 66 in the roller 54 cooperate to prevent any portion(s) of the container 20 from escaping from the applicator housing 12 via the dispensing end 23. Moreover, the openings 66 in the roller 54 allow movement of the skin sealant therethrough while greatly reducing or preventing any portion(s) of the container 20 from being expelled from the applicator 10. Therefore, the skin sealant 22 flows over and around the roller 54 via the slot 60 and through the roller 54 via the plurality of openings 66 therein so that the skin sealant 22 may be evenly and smoothly applied to a patient's prepped skin.

The dispensing end 23 prevents a user from causing abrasions on a patient's skin by pushing too hard on the applicator 10. The smooth ends 56 may curve slightly inward toward the roller 54. The roller 54 substantially fills the slot 60 and is positioned by the tapered portions 33 of the dispensing end 23 to extend slightly away from the dispensing end 23. Altenatively, the roller 54 is positioned at the same level as the smooth ends 56. Therefore, in either of these alternatives, no sharp portions of the applicator 10 are presented at the dispensing end 23 which would cause abrasions to a patient's skin. This smooth design of the components of the dispensing end 23 acts to substantially or completely prevent a force applied to the applicator 10 by a user during the application of the skin prep to a patient's skin from causing abrasion(s) to the patient's skin. In addition, the design of the components of the dispensing end 23 permit the skin sealant 22 to be spread evenly, quickly and uniformly by a user over the prepped skin of a patient.

Desirably, the components of the applicator 10 which are contacted by the skin sealant are formed from a material or materials which do not react with the skin sealant. The skin sealant may cure or harden within about three (3) minutes from the time it is released from the container 20.

The roller 54 and the dispensing end 23 of the applicator 10 permit the skin sealant 22 to be applied uniformly and relatively evenly over a rough skin surface. Such a rough skin surface includes, but is not limited to, a skin surface having sutures, staples, and so forth.

The regard to a skin sealant, one film former available in a skin sealant composition is commercially known as Integu-Seal® and is available from Medlogic Global, Ltd of Plymouth, England. InteguSeal® skin sealant contains medical grade n-butyl cyanoacrylate monomer (80% w/w). Medical grade cyanoacrylate is double distilled. Non-medical grade cyanoacrylate, in contrast, is single distilled and is typically marketed as a "super glue" type adhesive for gluing a wide variety of substrates together.

In addition to being used as a traditional skin sealant, i.e. as a film forming barrier through which a surgical incision is made, the skin sealant composition may also be used like a bandage to close and/or cover wounds, abrasions, burns, acne, blisters and other disruptions in the skin to protect them from subsequent contamination. The use of the skin sealant composition would therefore not be limited to medical personnel.

Wound protection is critical in permitting the healing process to take place. Traditional adhesive bandages and gauze wound dressings have been used by the consumer to treat/dress acute wounds or skin irritations. Such adhesive bandages are generally passive, in that they offer little or no chemical treatment for wound healing. Rather, they primarily serve to exert low levels of pressure on the wound, protect the wound from exposure to the environment, and absorb any exudates, which are produced from the wound site. Such bandages generally include a base layer, which is the layer seen by the consumer following application of the bandage to the wound. Such a layer is typically formed from a polymeric material such as a film, nonwoven web, or combination thereof, and may be perforated in some fashion to allow for flexibility and/or further breathability. This layer often includes a film component, having a top side surface which is seen by the consumer after application of the bandage to the wound site, and a bottom side surface (skin contacting surface). A skin-friendly adhesive is usually placed over the base layer bottom side surface to provide a means for attaching the bandage to the consumer. Alternatively, a separate adhesive tape is used to attach the bandage/wound dressing to the wound site, if the bandage/wound dressing is of the nonadhesive type. In the center of the base layer bottom side surface is traditionally positioned an absorbent pad for absorbing exudates from the wound. Finally, a non-stick perforated film layer is normally positioned over the absorbent pad layer, to provide a barrier between the absorbent pad and the wound itself. This allows the wound fluid to move through the perforated layer without sticking to the wound site. Typically the absorbent pad in such bandage does not include any medicinal components, although comparatively recently, bandage manufacturers have started including antibiotic agents on or within bandages to encourage wound healing.

The skin sealant composition of this invention can replace this seemingly complicated bandage construction with a single liquid treatment that will dry to a flexible coating that protects a wound much like a bandage would. Additionally, medicaments such as antibiotic agents may be blended in effective amounts with the composition to provide additional benefits in the area of microbial inhibition and the promotion of wound healing. The sealant may be applied to provide an effectively thick coating over the surface of the superficial wound, burn or abrasion. Because the to-be-treated wound is superficial and does not extend beyond the dermal layer, any polymeric residues diffusing into or forming in the wound will be naturally extruded from the skin. Generally, the sealant provides an adhesive film coating over the wound area which when set is satisfactorily flexible and adherent to the tissue without premature peeling or cracking. The coating generally has a thickness of less than about 0.5 millimeter (mm).

Sealant coatings of such thicknesses form a physical barrier layer over superficial wounds which provide protection for the wound in the same manner as a conventional bandage. Specifically, the coating provides an almost airtight, waterproof seal around the wound which does not need to be replaced when the wound gets wet. Once applied, the coating prevents bacterial and contaminant entry into the wound, thus reducing the rate of secondary infection. Generally, the adhesive coating does not limit dexterity and promotes faster wound healing. Additionally, unlike conventional bandages, the sealant naturally sloughs off the skin within 2-3 days after application and, accordingly, avoids the discomfort associated with removal of conventional bandages from the skin. However, if early removal of this polymeric coating is desired, such can be achieved by use of solvents such as acetone. Further discussion of this use may be found in U.S. Pat. No. 6,342,213.

By way of elaboration it should be noted that several wound care products are currently being marketed which contain an antiseptic benzalkonium chloride and an antibiotic mixture of polymixin B-sulfate and bacitracin-zinc. Patents in this area of technology have described the use of commonly known antiseptics and antibiotics, such as those described in U.S. Pat. Nos. 4,192,299, 4,147,775, 3,419,006, 3,328,259, and 2,510,993. U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate. U.S. Pat. No. 4,593,071 to Keough reported moisture cross-linkable ethylene copolymers having pendant silane acryloxy groups.

A polyurethane wound coating is described by Tedeshchl et al., in EP 0992 252 A2, where a lubricious, drug-accommodating coating is described that is the product of a polyisocyanate; an amine donor, and/or a hydroxyl donor; and an isocyanatosilane adduct having terminal isocyanate groups and an alkoxy silane. A water soluble polymer, such as poly(ethylene oxide), can optionally be present. Cross-linking causes a polyurethane or a polyurea network to form, depending upon whether the isocyanate reacts with the hydroxyl donors or the amine donors. U.S. Pat. No. 6,967,261 describes the use of chitosan in wound treatment. Chitosan is a deacetylated product of chitin $(C_8 H_{13} NO_5)_n$, an abundant natural glucosamine polysaccharide. In particular, chitin is found in the shells of crustaceans, such as crabs, lobsters and shrimp. The compound is also found in the exoskeletons of marine zooplankton, in the wings of certain insects, such as butterflies and ladybugs, and in the cell wall of yeasts, mushrooms and other fungi. Antimicrobial properties of chitosan have been reported against Gram positive and Gram negative bacteria, including *Streptococcus* spp., *Staphylococcus aureus*, *Staphylococcus epidermidis*, *Staphylococcus haemolyticus*, *Pseudomonas*, *Escherichia*, *Proteus*, *Klebsiella*, *Serratia*, *Acinobacter*, *Enterobacter* and *Citrobacter* spp. Chitosan has also been described in the literature to induce repair of tissue containing regularly arranged collagen bundles.

The composition may also be used to close wounds much like stitches or bandages. To be used in such a way, the composition is applied to at least one skin surface of the opposed skin sections of, for example, a suturable wound of a mammalian patient (e.g., human patient). The opposed skin sections are contacted with each either before or after application of the composition. In either case, after application of the composition, the wound area is maintained under conditions wherein the composition polymerizes to join these skin sections together. In general, a sufficient amount of the composition may be employed to cover the wound and the adjacent the skin surface of at least one of the opposed skin sections of the suture-able or staple-able wound. Upon contact with skin moisture and tissue protein, the composition will polymerize or, in the case of compositions utilizing partially polymerized monomers, will further polymerize, at ambient conditions (skin temperature) over about 10 seconds to 60 seconds to provide a solid polymeric film which joins the skin sections, thereby closing the wound. Generally, the composition can provide a polymeric film over the separated skin sections thereby inhibiting infection of the wound while promoting healing. Further discussion of this use may be found in U.S. Pat. No. 6,214,332.

The composition may be packaged in a "kit" form for use in medical facilities and bundled with the appropriate skin prep solution for ease of use and the convenience of the medical personnel. Kits may also include a container holding the skin sealant composition and an applicator. Alternatively the skin sealant container is contained within the applicator. In addition, various complimentary or "mating" containers and different packaging schemes have been used for some time and are known in the art.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An applicator for a skin sealant, comprising:
an applicator housing formed to include an internal compartment configured to hold a container of skin sealant, the housing including a dispensing end having at least one opening formed therethrough, the housing including an actuator configured to contact the container and release the skin sealant therefrom, the dispensing end having at least one movable member such that the dispensing end is flexible and is configured to move on more than one axis when the dispensing end is positionable against a patient's skin, the dispensing end further comprising a porous roller having a plurality of openings formed therethrough, the roller rotatably held by the dispensing end of the housing, wherein when the skin sealant is released from the container, it flows through the plurality of openings in the roller and the at least one opening surrounding the roller in the dispensing end, wherein the roller is positioned so that when the roller on the dispensing end of the applicator is adapted to be stroked against a patient's skin, the skin sealant flows around and through at least a portion of the roller such that the skin sealant is uniformly dispensable on a patient's skin via the roller, and wherein pressure applied to the roller and the dispensing end by a user for applying the skin sealant on a patient's skin does not result in abrasions on the patient's skin.

2. The applicator of claim 1, wherein the movable member further comprises a detent.

3. The applicator of claim 2, wherein the movable member further comprises a detent extending about the dispensing end.

4. The applicator of claim 3, wherein the movable member further comprises a plurality of detents.

5. The applicator of claim 2, wherein the movable member further comprises a convexity.

6. The applicator of claim 1, wherein the movable member comprises a convexity.

7. The applicator of claim 6, wherein the movable member further comprises a convexity extending about the dispensing end.

8. The applicator of claim 7, wherein the movable member further comprises a plurality of detents.

9. The applicator of claim 1, wherein the movable member further comprises at least one detent and at least one convexity.

10. The applicator of claim 1, wherein the actuator is moveable.

11. The applicator of claim 10, wherein the actuator comprises a plunger.

12. The applicator of claim 10, wherein the actuator comprises a button.

13. The applicator of claim 10, wherein actuator comprises a latch or lever.

14. The applicator of claim 10, wherein the actuator comprises a portion of the housing.

15. The applicator of claim 1, wherein the dispensing end includes a sponge therein.

16. The applicator of claim 1, wherein the dispensing end is configured to move in more than two axes.

17. The applicator of claim 16, wherein the dispensing end is configured to move in three axes.

18. The applicator of claim 1, wherein the roller comprises a cylindrical shape.

19. The applicator of claim 1, wherein the roller comprises a spherical shape.

20. The applicator of claim 1 wherein the roller comprises an elliptical shape.

21. The applicator of claim 1, wherein the roller is positioned at substantially the same level as the dispensing end.

22. The applicator of claim 1, wherein the roller extends outward and away from the dispensing end.

23. An applicator for a skin sealant, comprising:
an applicator housing formed to include an internal compartment configured to hold a container of skin sealant, the housing including a dispensing end having at least one opening formed therethrough, the housing including an actuator configured to contact the container and release the skin sealant therefrom, the dispensing end having at least one movable member such that the dispensing end is flexible and is configured to move on up to three axes sequentially or simultaneously, wherein the dispensing end further comprises a porous roller having a plurality of openings formed therethrough, the roller rotatably held by the dispensing end of the housing, wherein when the skin sealant is released from the container, it flows through the plurality of openings in the roller and the at least one opening surrounding the roller in the dispensing end, wherein the roller is positioned so that when the roller on the dispensing end of the applicator is adapted to be stroked against a patient's skin, the skin sealant flows around and through at least a portion of the roller such that the skin sealant is smoothly dispensable on a patient's skin via the roller, and wherein pressure applied to the roller and the dispensing end by a user for applying the skin sealant on a patient's skin does not result in abrasions on the patient's skin.

24. The applicator of claim 23, wherein the roller is positioned at substantially the same level as the dispensing end.

25. The applicator of claim 23, wherein the roller extends outward and away from the dispensing end.

* * * * *